United States Patent [19]

Bright

[11] Patent Number: 4,470,909

[45] Date of Patent: Sep. 11, 1984

[54] EXTRACTION OF HALOCARBONS FROM AQUEOUS SOLUTIONS

[75] Inventor: John H. Bright, Kendall Park, N.J.

[73] Assignee: American Cyanamid Company, Stamford, Conn.

[21] Appl. No.: 429,906

[22] Filed: Sep. 30, 1982

[51] Int. Cl.$^3$ .............................................. C02F 1/26
[52] U.S. Cl. .................................... 210/634; 210/679; 210/908; 210/909
[58] Field of Search ................ 210/679, 691, 908, 909, 210/634, 633

[56] References Cited

U.S. PATENT DOCUMENTS

| | | | |
|---|---|---|---|
| 3,708,462 | 1/1973 | McKinley et al. | 526/274 |
| 3,906,762 | 6/1976 | Kroebel et al. | 210/656 |
| 4,042,498 | 8/1977 | Kennedy | 210/909 |
| 4,224,415 | 9/1980 | Meitzner et al. | 526/89 |
| 4,276,179 | 6/1981 | Soehngen | 210/679 |

FOREIGN PATENT DOCUMENTS

| | | | |
|---|---|---|---|
| 50-81965 | 7/1975 | Japan | 210/679 |
| 53-101847 | 9/1978 | Japan | 210/691 |

*Primary Examiner*—Peter A. Hruskoci
*Attorney, Agent, or Firm*—Michael J. Kelly

[57] ABSTRACT

A method for removing halogenated hydrocarbons from water is disclosed. The method comprises contacting said aqueous solution with a phosphine oxide either alone or on a solid support.

12 Claims, No Drawings

EXTRACTION OF HALOCARBONS FROM AQUEOUS SOLUTIONS

The present invention relates to a method for the extraction of halogenated hydrocarbons from aqueous solutions containing them. More particularly, it relates to a method for the extraction of chlorinated aliphatic and aromatic compounds from aqueous solutions using phosphine oxides on inert solid supports as the extractant. Still more particularly, it relates to a method for the removal of halogenated hydrocarbons from the drinking water supply system.

A concern among environmental and public health authorities is the significance of potential contamination of the water supply system by halogenated hydrocarbons from industrial processes. Some investigations have expressd a particular concern for the drinking water supply because some halogenated hydrocarbons, e.g., PCB's (polychlorinated biphenyls), are fat soluble and, over time, may present a serious health problem. At present there is no readily available, economical method for removing these compounds from aqueous solutions.

In accordance with the present invention there is provided a method for the removal, by extraction, of halogenated hydrocarbons, particularly chlorinated hydrocarbons, from aqueous solutions, which comprises contacting an aqueous solution containing them with a phosphine oxide compound alone or supported on a solid, inert carrier material, hereinafter also referred to as the support.

Phosphine oxides which are useful in accordance with the present invention are those represented by the formula:

$$R_3P=O$$

wherein R represents, individually, alkyl, cycloalkyl, aralkyl and substituted aralky. Preferred alkyls included about $C_6$ to about $C_{18}$ straight and branched chain alkyls while preferred cycloalkyls include six carbon to eight carbon substituted and unsubstituted cycloalkyls.

Examples of suitable phosphine oxides include, but are not limited to, tri-n-hexylphosphine oxide (THPO), tri-n-octyl-phosphine oxide (TOPO), tris(2,4,4-trimethylpentyl)phosphine oxide, tricyclohexylphosphine oxide, tri-n-dodecylphosphine oxide, tri-n-octadecylphosphine oxide, tris(2-ethylhexyl)phosphine oxide, di-n-octylethylphosphine oxide, di-n-hexylisobutylphosphine oxide, octyldiisobutylphosphine oxide, tribenzylphosphine oxide, di-n-hexylbenzylphosphine oxide, di-n-octylbenzylphosphine oxide, 9-octyl-9-phosphabicyclo[3.3.1]nonane-9-oxide, and the like, and mixtures thereof. TOPO and THPO are preferred, singly or in mixtures.

Halogenated hydrocarbons which are subject to extraction from aqueous solutions by present process of the invention include, but are not limited to, aliphatic and aromatic halogenated hydrocarbons, represented by the following types: $CX_4$, $CX_3CX_3$, $CX_2=CX_2$, wherein X represents hydrogen or a halogen atom, provided at least one X is a halogen atom; compounds represented by the formula:

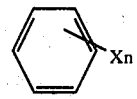

wherein X represents a halogen atom and n is an integer from 1 to 6; and compounds represented by the formula:

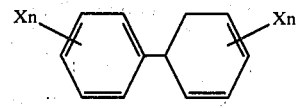

wherein X represents a halogen atom and n is an integer from 1 to 5.

Representative examples of halogenated hydrocarbons which are extracted from aqueous solutions according to the method of the present invention include, but are not limited to, dichloromethane, dibromomethane, trichloromethane, tribromomethane, bromoethane, bromopropane, 1,1,1-trichloroethane, 1,1,2-trichloroethane, tetrachloromethane, 1,1,1-tribromoethane, 1,1,2-tribromoethane, 1,1,2-trichloroethylene, 1,1,2,2-tetrachloroethylene, 1,2-dibromoethane, chlorobenzene, bromobenzene, o-dichlorobenzene, o-dibromobenzene, m-dichlorobenzene, p-dichlorobenzene, chlorinated biphenyls, brominated biphenyls, chlorinated naphthalenes, and the like, and mixtures thereof, and corresponding fluoro and iodo compounds.

While the phosphine oxide may be used alone, especially if it is in the form of a solid or semi-solid, it is particularly more convenient if it is supported on a solid carrier or support. While in general the support will be inert, the present invention is not limited to inert supports and chemically active supports may be used where it is desired to extract materials unextractable by the phosphine oxide.

The solid materials or supports for the phosphine oxide extractants of the present invention are preferably waterinsoluble absorbents and include, but are not limited to, such materials as diatomaceous earth, silica, wide-pore carbon, and the like, or crosslinked polymeric materials in the form of porous beads. Synthetic macroporous, crosslinked copolymers of styrene and divinyl benzene are commonly used support materials. Other commonly used supports are, for example, divinylbenzene crosslinked polyacrylates and polymethacrylates. These supports themselves are generally not critical and a convenient support amenable to a particular application may easily be determined by one skilled in the art with simple experimentation.

Many monovinyl compounds (monomers) can be used alone or combined in the preparation of the polymeric supports useful in the present invention. They include, but are not limited to, styrene, methylstryrene, acrylic acid, methacrylic acid, acrylonitrile, vinyl anisole, vinyl naphthalene; acrylic and methacrylic acid esters, such as methyl-, ethyl-, propyl-, isopropyl-, butyl-, isobutyl-, tert.butyl-, ethylhexyl-, cyclohexyl-, benzyl-, phenyl-, ethoxymethyl-, propoxymethyl-, propoxypropyl-, ethoxyphenyl-, ethoxybenzyl-, ethoxycyclohexyl-, methoxycyclohexyl acrylates and methacrylates; alkylphenyl acrylates and methacrylates; ethylene, propylene, isobutylene, diisobutylene; vinyl chloride, vinyl acetate, vinylidene chloride, and the like.

Polyethylenically unsaturated monomers, such as butadiene, isoprene, chloroprene, which behave as if they had only a simple double bond, are also suitable.

Suitable polyvinyl compounds which function as crosslinking agents include, but are not limited to, divinylbenzene, divinylpyridine, divinyltoluene, divinylnapthalene, diallyl phthalate, ethyleneglycol diacrylate, ethyleneglycol dimethacrylate, divinylxylene, divinylethylbenzene, divinylsulfone, polyvinyl- or polyallyl ethers of glycols, glycerine and pentaerythritol, divinylketone, divinyl sulfide, allylacrylate, diallylmaleate, diallylfumarate, diallyl succinate, diallyl carbonate, diallyl malonate, diallyl oxalate, diallyl adipate, diallyl sebacate, divinyl sebacate, diallyl silicate, triallyl phosphate, N,N'-methylenediacrylamide,N,N'-methylenedimethacrylamide, N,N'-ethylenediacrylamide, trivinylvenzene, trivinylnaphthalene, and the like. The amount of polyvinyl compound used may vary over wide limits. In general, however, the polyvinyl compound is used in an amount ranging from about 5 to 70% by weight, based on the total weight of monomers, and preferably between about 8 and 60% by weight.

The phosphine oxide extractant compound may be incorporated in or on the support material by any convenient technique. Conventional and applicable techniques include, but are not limited to, impregnation, with the aid of a solvent, or by encapsulation, through the addition of the extractant to the monomer mixture, adding a polymerization catalyst, and then polymerizing the resulting mixture or solution of monomers in the presence of the extractant by conventional techniques. A procedure for the encapsulation of extractants via this technique is described by Krobel et al, U.S. Pat. No. 3,960,762.

In addition to the polymeric cross-linked macroporous polymers described above, the present invention may utilize as the polymeric support material crosslinked macroporous copolymers containing phosphine oxide functions directly bonded to the polymer backbone. An example of such a polymer is a copolymer of styrene, chloromethyl styrene and divinylbenzene or a copolymer of p-chloromethyl styrene and divinylbenzene wherein the chloromethyl group is reacted with a secondary phosphine oxide, e.g., dioctylphosphine oxide; see, for example, European Patent Application No. 0031761 to Bolleau et al. Similar polymers are described by McKinley et al, U.S. Pat. No. 3,708,462.

Alternatively, certain crystalline phosphine oxides, such as tribenzylphosphine oxide, may be used alone, or mixed with an inert solid material, as a support for extraction of halocarbons. Thus, a solution containing halocarbons to be extracted may be slurried with the solid phosphine oxide or passed through a column packed with the solid phosphine oxide or a mixture thereof with an inert solid material.

The amount of phosphine oxide incorporated in or on the support material by impregnation or encapsulation, or by the use of polymers containing phosphine oxide groups, or by the use of crystalline phosphine oxides alone, may vary over wide limits, provided sufficient phosphine oxide is available to extract the halocarbons from solutions containing them. Ordinarily, the need for efficiency of extraction will determine the amount of phosphine oxide extractant used and these levels can easily be determined by one skilled in the art with simple experimentation.

The following examples are provided by way of illustration and are in no way limiting of the scope of the invention which is capable of wide variance and application within the scope of the claims that follow. All parts and percentages are by weight unless otherwise indicated.

EXAMPLE 1

Preparation of Supported TOPO Extractant

Divinylbenzene crosslinked macroporous polystyrene beads (Aldrich Chem. Co.), 24.1 grams, were added to a solution of 12.1 grams of tri-n-octylphosphine oxide (TOPO) in 100 ml. of toluene. The mixture was stirred and heated for about 30 minutes on a steam bath and the toluene was then removed under vacuum. The polymer beads, containing 33.4% TOPO, were dried at 95° C./0.1 torr.

EXAMPLE 2

Preparation of Supported TOPO/THPO Extractant

Diatomaceous earth (Gas-Chrom. 60/80-mesh, Applied Science Laboratories), 60 grams, was added to a solution of 15 grams of a mixture of 27.8% TOPO and 72.2% THPO (tri-n-hexylphosphine oxide) in 200 ml. of petroleum ether. The mixture was stirred and heated to 95° C. and the petroleum ether removed in vacuo. Diatomaceous earth containing 20% of the mixed phosphine oxides was obtained after a final drying at 95° C./0.1 torr.

EXAMPLE 3

A column was prepared containing 30 grams of the polystyrene supported extractant of Example 1. A sample of 40 ml. of demineralized water (Millipore) was passed through the column and collected (Control Sample No. 1). Then, an aqueous solution (41 ml.) containing a mixture of:

trichloromethane
1,1,1-trichloroethane
1,1,2-trichloroethane
1,1,2-trichloroethylene
dichloromethane was passed through the column and samples collected after 100 minutes and 125 minutes (Effluent Samples No. 2 and 3, respectively, according to EPA Protocol).

In a similar manner the solution was passed through a column containing untreated polystyrene beads and a sample (Effluent Sample No. 4) was collected.

Analyses of Control Sample No. 1 and Effluent Samples 2, 3 and 4 for chlorohydrocarbon content by gas chromatography-mass spectrometry, according to EPA recommended methodology, were as follows:

| Control Sample No. 1: | 5-10 ppb dichloromethane; other chlorohydrocarbons <5 ppb. |
|---|---|
| Effluent Sample No. 2: | 5-10 ppb dichloromethane; other chlorohydrocarbons <5 ppb. |
| Effluent Sample No. 3: | 5-10 ppb dichloromethane; other chlorohydrocarbons <5 ppb. |
| Effluent Sample No. 4: | trichloromethane 19 ppm |
| | 1,1,1-trichloroethane 2 ppm |
| | 1,1,2-trichloroethane 2 ppm |
| | 1,1,2-trichloroethylene 1 ppm |
| | dichloromethane 34 ppm |

The data obtained in Example 3 are summarized in Table I.

TABLE I

Extraction of chlorohydrocarbons with TOPO on Macroporous Divinylbenzene-Crosslinked Polystyrene Beads

| Aqueous Feed Solution (Mixture) | Initial Conc. (ppm) | Effluent Conc. (Supported TOPO) | Effluent Conc. Control |
|---|---|---|---|
| Trichloromethane | 186 | <5 ppb | 19 ppm |
| 1,1,1-Trichloroethane | 205 | <5 ppb | 2 ppm |
| 1,1,2-Trichloroethane | 212 | <5 ppb | 2 ppm |
| 1,1,2-Trichloroethylene | 107 | <5 ppb | 1 ppm |
| Dichloromethane | 114 | 5–10 ppb | 34 ppm |

EXAMPLE 4

A column was prepared containing 22 grams of the diatomaceous earth supported extractant of Example 2. A sample of demineralized water (Millipore) was passed through the column and collected (Control Sample No. 5). Then, 41 ml. of the aqueous solution containing chlorohydrocarbons, described in Example 3, was passed through the column and samples collected after 85 minutes and 120 minutes. (Effluent Samples 6 and 7, respectively, according to EPA protocol).

In a similar manner, the solution was passed through a column containing untreated diatomaceous earth and a sample (Effluent Sample 8) was collected.

The several samples were analyzed, as described in Example 3, with the following results:

Control Sample No. 5: 5–10 ppb dichloromethane; other chlorohydrocarbons <5 ppb

Effluent Sample 6 and 7: 5–10 ppb dichloromethane; other chlorohydrocarbons <5 ppb Effluent Sample 8: No chlorohydrocarbons extracted The data obtained in Example 4 are summarized in Table II.

TABLE II

Extraction of Chlorohydrocarbons with TOPO/THPO on Diatomaceous Earth

| Aqueous Feed Solution | Initial Conc. (ppm) | Effluent Conc. (Supported TOPO/THPO) | Effluent Conc. (Control) |
|---|---|---|---|
| Trichloromethane | 186 | <5 ppb | 186 ppm |
| 1,1,1-Trichloroethane | 205 | <5 ppb | 205 ppm |
| 1,1,2-Trichloroethane | 212 | <5 ppb | 212 ppm |
| 1,1,2-Trichloroethylene | 107 | <5 ppb | 107 ppm |
| Dichloromethane | 114 | 5–10 ppb | 114 ppm |

The data obtained in Examples 3 and 4 and summarized in Tables I and II indicate that TOPO or TOPO/THPO, supported on either divinylbenzene-crosslinked polystyrene or diatomaceous earth, are very efficient extractants for chlorohydrocarbons. Crosslinked polystyrene beads (untreated) does extract chlorohydrocarbons; see Effluent Sample 4. However, the extraction is not efficient, and the levels of chlorohydrocarbons, especially chloroform, exceeds the EPA required maximum level of 0.1 ppm for trihalomethanes in drinking water. It is also clear from the data (Effluent Sample 8) that untreated diatomaceous earth has no extractive capacity whatsoever.

EXAMPLE 5

Extraction of Perchloro-aliphatic and Chloroaromatic hydrocarbons

A. A column containing 33% by weight of TOPO on diatomaceous earth (Celite 566, Johns Manville), was prepared according to the procedure of Example 4. An aqueous solution containing a mixture of chlorohydrocarbons:

carbon tetrachloride
1,1,2,2-Tetrachloroethylene
Chlorobenzene
o-,m-,p-dichlorobenzene to the extent of their solubilities in water, was passed through the column. The concentration of the several chlorohydrocarbons in the effluent was determined, as described in Examples 3 and 4, and expressed as a percentage of the initial solution. Data are given in Table III.

B. In a manner similar to (A) above, the solution was passed through a column containing 33% by weight of triphenylphosphine oxide (TPPO) on diatomaceous earth (Celite 566). Data are given in Table IV.

TABLE III

Extraction of Chlorinated Aliphatic and Chlorinated Aromatic Hydrocarbons with TOPO on Diatomaceous Earth

| Aqueous Feed Solution | Effluent Conc. (Supported TOPO, % of Original Solution) | Effluent Conc. (Untreated Support, % of Original Solution) |
|---|---|---|
| Carbon Tetrachloride | 0.06;  0.16 | 47; 57 |
| 1,1,2,2-Tetrachloroethylene | 0.002;  0.005 | 84; 66 |
| Chlorobenzene | 0.005;  0.015 | ~100; 100 |
| o-Dichlorobenzene | <0.001 | 92; 97 |
| m-Dichlorobenzene | <0.001 | 92; 97 |
| p-Dichlorobenzene | <0.001 | 92; 97 |

TABLE IV

| Aqueous Feed Solution | Effluent Conc. (Supported TPPO, % of Original Solution |
|---|---|
| Carbon Tetrachloride | 71; 71 |
| 1,1,2,2-Tetrachloroethylene | 65; 67 |
| Chlorobenzene | 74; 79 |
| o-Dichlorobenzene | 61; 82 |
| m-Dichlorobenzene | 61; 82 |
| p-Dichlorobenzene | 61; 82 |

Data shown in Tables III and IV indicate that TOPO on diatomaceous earth is a very efficient extractant for a variety of perchloroaliphatic and chloroaromatic hydrocarbons; that TPPO on diatomaceous earth is not effective as an extractant for these compounds; and that diatomaceous earth (untreated) is an inefficient extractant for perchloroaliphatics and has virtually no affinity for chloroaromatics.

EXAMPLE 6

A sample of silica gel (Aldrich, Grade 15) containing 33% by weight of TOPO, prepared according to the procedure of Example 4, was slurried in an aqueous solution containing 500–600 ppb of Arochlor 1254 (Monsanto), which is a mixture of chlorinated biphenyls (PCB's). The solution was filtered and analyzed by gas chromatography—Mass spectrometry. Data are given below.

| Initial PCB Conc., ppb | PCB Conc. of Aqueous Extracts ppb | |
|---|---|---|
|  | TOPO on Silica Gel | Silica Gel, Control |
| 516 | 164 | 599 |

The data indicate that TOPO on Silica gel is effective in extracting PCB's from aqueous solution, whereas untreated silica gel is totally ineffective.

EXAMPLE 7

Extension of Scope to Other Halocarbons

Tables 7A to 7C as follows are compilations of the extractions of a mixture of aqueous octafluoronaphthalene, trichloroethylene, 1,2-dibromoethane, and iodomethane with three supported columns: 7A—blank diatomaceous earth; 7B—30 weight percent impregnated TOPO on diatomaceous earth; and 7C—30 weight percent TPPO impregnated on diatomaceous earth.

By 47 ml of effluent through the blank column, a break-through of all four halogen compounds has occurred. By 144 mls, the effluent flow concentration is virtually the same as the feed.

The TPPO column shows a break-through for three of the halogenohydrocarbons, excepting the fluoro-, by 30 ml of effluent. The fluoro-compound breaks through between 56 and 107 ml effluent. Thus, the TPPO column shows similar low extraction activity to the blank column for chloro-, bromo-, and iodo-components. Activity is found, however, for the fluoro-compound.

The TOPO column shows substantial activity for the fluoro- and chloro-compounds with extraction occurring at 246 ml effluent. Good extraction of the bromo compound is demonstrated since the break-through is evidenced at 140 ml (3.7 ppm). The 140 ml volume is considerably more than <47 ml break-through (22 ppm) bby the TPPO column.

Iodomethane is extracted to a lesser extent than in the case of the other halogens. Some extraction has occurred with the TOPO column as the break-through shows between 43 and 93 mls. The blank and TPPO columns have broken through by 47 and 30 ml, respectively.

This example makes it clear that specific extraction profiles could easily be obtained by proper selection of particular oxides and mixtures thereof which selection and combination should easily be determined by simple experimentation.

TABLE 7A

Extraction of Aqueous Halogenohydrocarbons by Blank Diatomaceous Earth

| | Effluent Concentration, ppm | | | |
|---|---|---|---|---|
| Effluent Volume ml | Octafluoro-naphthalene | Trichloro-ethylene | 1,2-Di-bromo-ethane | Iodo-methane |
| Initial Feed Concentration | 2.2 | 18 | 23 | 17 |
| 47 | 1.4 | 16 | 20 | 17 |
| 90 | 1.9 | 16 | 20 | 16 |
| 144 | 2.3 | 18 | 23 | 18 |

TABLE 7B

Extraction of Aqueous Halogenohydrocarbons by 30 Wt % TOPO Impregnated on Diatomaceous Earth

| | Effluent Concentration, ppm | | | |
|---|---|---|---|---|
| Effluent Volume ml | Octafluoro-naphthalene | Trichloro-ethylene | 1,2-Di-bromo-ethane | Iodo-methane |
| Initial Feed Concentration | 2.4 | 20 | 24 | 20 |
| 18 | 0.03 | 0.1 | N.D. | 2 |
| 43 | 0.02 | 0.1 | N.D. | 2 |
| 93 | 0.02 | 0.1 | N.D. | 17 |
| 140 | 0.02 | 0.1 | 3.7 | 17 |
| 246 | 0.2 | 0.1 | 20 | 17 |

N.D. = none detected <0.05 ppm

TABLE 7C

Extraction of Aqueous Halogenohydrocarbons by 30 Wt % TPPO Impregnated on Diatomaceous Earth

| | Effluent Concentration, ppm | | | |
|---|---|---|---|---|
| Effluent Volume ml | Octafluoro-naphthalene | Trichloro-ethylene | 1,2-Di-bromo-ethane | Iodo-methane |
| Initial Feed Concentration | 2.5 | 19 | 23 | 20 |
| 30 | 0.15 | 17 | 22 | 18 |
| 56 | N.D. | 19 | 23 | 20 |
| 107 | 1.8 | 16 | 21 | 16 |

N.D. = none detected <0.05 ppm

EXAMPLE 8

Several polymeric extractants were prepared as described below.

A. Hollow Macroporous Styrene-Divinylbenzene Copolymer (15% crosslinking). A solution of 72.75 grams of styrene, 27.25 grams of divinylbenzene (55%, the remainder being polymerizable monomers), 1.0 gram of azobixisobutyronitrile and 43 grams of toluene was added to a solution of 2 grams of the ammonium salt of a styrene-maleic anhydride polymer. The mixture was stirred under nitrogen for 15 hours at 80° C., the resulting beads were filtered, washed with water and dried at 72° C.

B. Macroporous Styrene-Divinylbenzene Copolymer Containing Encapsulated Tri-n-Octylphosphine Oxide. The procedure of A was followed except that 43 grams of tri-n-octylphosphine oxide was used in place of toluene. The resulting polymer beads contained 30% phosphine oxide.

C. Macroporous Styrene-Divinylbenzene Copolymer Containing Chemically Bound Phosphine Oxides.

(I) A solution of 30 grams of p-chloromethylstyrene, 14 grams of styrene, 6 grams of divinylbenzene (55%), 0.55 gram of azobisisobutyronitrile and 50 grams of toluene was added to a solution of 1 gram of polyvinylpyrrolidone in 400 grams of water. The mixture was stirred at 80° C. under nitrogen for 19 hours and the resulting beads were isolated, washed with water and dried at 72° C.

The polymer beads (10 grams) were suspended in 30 ml of dimethyl formamide to which was added 2.5 grams of potassium hydroxide, 3 grams of methanol and 38 grams of dimethyl formamide. Di-n-hexylphosphine oxide (10 grams) and 0.4 gram of potassium hydroxide were added and the mixture was stirred under nitrogen for 18 hours. The resulting beads were filtered, washed with water and dried. The beads contained 1.16% P.

II. Following the procedure of I except that 8.75 grams of dicyclohexylphosphine oxide was used instead of 10 grams of di-n-hexylphosphine oxide, beads were obtained containing 0.92% P.

Columns were separately prepared containing 10 grams of the polymers of A and B and 9.5 grams of the polymer of C, which consisted of
3.9 grams I
6.4 grams II
which had 1.01% P.

Table 8 shows the extraction of high concentrations of chloroform in water (244–310 ppm) by the several extractants. The hollow beads (polmer A) exhibited modest activity, but poor loading, i.e., after 1185 ml of the 244 ppm solution of chloroform was passed through the column, only 0.002 gram per gram of resin was extracted. Polymer B, containing 30% encapsulated TOPO, shows substantial activity, having extracted 0.0292 gram per gram of resin from 1136 ml of 310 ppm chloroform solution, or 14.6 times the loading of Polymer A. The phosphorus bound polymer also exhibits good loading, having extracted 0.0093 grams per gram of resin from 1144 ml of 275 ppm chloroform solution or 4.6 times the loading of Polymer A.

TABLE 8

Extraction of Aqueous Chloroform by Blank Divinylbenzene Crosslinked Macroporous Polystyrene, 30 wt % Encapsulated TOPO In Similar Polystyrene, and Phosphine Oxide Reacted Polystyrene (P = 1.01 Wt %)

| Hollow Column, 10g 224 ppm CHCl$_3$ Feed | | 30% Encapsulated TOPO, 10g 310 ppm CHCl$_3$ Feed | | Bound Phosphine Oxide (P = 1.01) 9.5g 275 ppm CHCl$_3$ Feed | |
|---|---|---|---|---|---|
| Effluent | CHCl$_3$ | Effluent | CHCl$_3$ | Effluent | CHCl$_3$ |
| ml | CHCl$_3$, ppm | Loading g/g | ml | CHCl$_3$, ppm | Loading g/g | ml | CHCl$_3$, ppm | Loading g/g |

| ml | CHCl$_3$, ppm | Loading g/g | ml | CHCl$_3$, ppm | Loading g/g | ml | CHCl$_3$, ppm | Loading g/g |
|---|---|---|---|---|---|---|---|---|
| 32 | 5 | 0.0008 | 60 | 5 | 0.0018 | 26 | 15 | 0.00014 |
| 115 | 200 | 0.0019 | 110 | 10 | 0.0034 | 91 | 126 | 0.0021 |
| 215 | 248 | 0.0020 | 207 | 18 | 0.0062 | 185 | 158 | 0.0035 |
| | | | 427 | 35 | 0.0125 | 431 | 209 | 0.0058 |
| | | | 690 | 54 | 0.0194 | | | |
| 1185 | 244 | 0.0020 | 1136 | 125 | 0.0292 | 1144 | 249 | 0.0093 |
| | | | 1564 | 190 | 0.0358 | | | |

EXAMPLE 9

Preparation of Macroreticular Styrene-Divinylbenzene Resin Containing Encapsulated TOPO(Method of Meitzner U.S. Pat. No. 4,224,415)

The following were prepared:
A.
  120 grams water
  0.24 gram ammonium salt of styrene-maleic anhydride copolymer
  4.5 grams sodium chloride
B.
  69.84 grams styrene
  26.16 grams divinylbenzene (15% of monomer mixture)
  80.00 grams tert.amylalcohol (45% of monomers & TAA)
  64.00 grams TOPO (40%)
  1.2 grams azobisisobutyronitrile (AIBN) catalyst B was added to A at a rate of agitation of 300 rpm and the temperature was raised to 80° C. The addition required about 2 hours and the resulting polymer beads were stirred at high speed (1000 rpm) for several hours. Water (60 grams) and sodium chloride (2.25 grams) were added. The beads were filtered, washed with water and dried; 110 grams of 131 grams total has bead size of ~30 mesh.

EXAMPLE 10

Preparation of Hollow Macroreticular Styrene-Divinylbenzene Resin (TOPO omitted); Method of Meitzner, U.S. Pat. No. 4,224,415

The procedure of Example 9 was followed except that TOPO was omitted. This polymer was used as a control in the following experiments.

EXAMPLE 11

The resin of Example 9, containing 40% TOPO, was charged to a column (210×12 mm, 9 grams of resin used). An aqueous solution containing 178 ppm of chloroform and another solution containing 22.6 ppm of 1,2-dibromoethane were passed through the column at a rate of 39 ml/hr. Data are given in Table 11A. In a similar way, a column was charged with the resin of Example 10 (Control); bed was 165×12 mm, 9 grams of resin. Similar solutions containing 196 ppm of chloroform and 23.5 ppm of 1,2-dibromoethane were passed through the column at a rate of 24 ml/hr. Data are given in Table 11B.

TABLE 11A

Extraction of Chloroform (178 ppm) and 1,2-Dibromoethane (22.6 ppm) from Aqueous Solution by a 40 Wt % TOPO Encapsulated in Crosslinked Macroreticular Polystyrene Column 9g 210 × 12 mm Packing: flow rate 39 ml/hr

| Cumulative Effluent mls | Effluent Concentration | |
|---|---|---|
| | Chloroform, ppm | 1,2-Dibromoethane, ppm |
| 31 | 0.24 | <0.01 |
| 116 | 0.24 | <0.01 |
| 268 | 0.30 | <0.01 |
| 725 | 2.6 | <0.01 |
| 895 | 15.3 | 0.15 |
| 1108 | 40.3 | 0.55 |
| 1810 | 159.7 | 5.8 |
| 1906 | 157.2 | 7.3 |
| 2080 | 182.0 | 10.7 |

TABLE 11B

Extraction of Chloroform (196 ppm) and 1,2-Dibromoethane (23.5 ppm) from Aqueous Solution by a Hollow Crosslinked Macroreticular Polystyrene Column 9g 165 × 12 mm Packing: flow rate 34 ml/hr

| Cumulative Effluent mls | Effluent Concentration | |
|---|---|---|
| | Chloroform, ppm | 1,2-Dibromoethane, ppm |
| 36 | 0.41 | 0.02 |
| 124 | 46.5 | 1.01 |
| 258 | 116.0 | 4.7 |
| 373 | 141.9 | 6.3 |

TABLE 11B-continued

Extraction of Chloroform (196 ppm) and 1,2-Dibromoethane (23.5 ppm) from Aqueous Solution by a Hollow Crosslinked Macroreticular Polystyrene Column 9g 165 × 12 mm Packing: flow rate 34 ml/hr

| Cumulative Effluent mls | Effluent Concentration | |
|---|---|---|
| | Chloroform, ppm | 1,2-Dibromoethane, ppm |
| 1079 | 188.8 | 9.0 |
| 1534 | 192.8 | 9.4 |

It is apparent when the data for extraction of chloroform in Tables 11A and 11B are compared that at a given break-through concentration (10 ppm), between 30 and 37 bed volumes (~24 cc, Table 11A) of solution were treated with the TOPO-containing resin, whereas only about 2 bed volumes (~18.7 cc, Table 11B) were treated with the control resin before break-through. This indicates that the TOPO-encapsulated resin is much more efficient than the control resin. Similar data are shown for 1,2-dibromoethane (~50 bed volumes vs. 6 bed volumes to a break-through concentration of 1 ppm.

EXAMPLE 12

Solvent Extraction Using 100% Liquid Tertiary Phosphine Oxide (Neat)

A mixture of 71.3 weight percent tri-n-hexyl- and 28.7 weight percent tri-n-octyl phosphine oxide was prepared. This mixture is a liquid at room temperature. Ten mls (8.9 grams) of the liquid mixture was contacted (with agitation) for 15 minutes with 100 ml of an aqueous solution containing 271 ppm chloroform and 29 ppm of 1,2-dibromoethane. After extraction, the aqueous solution contained 58 ppm chloroform and 7.1 ppm 1,2-dibromoethane.

What is claimed is:

1. A method for removing halogenated hydrocarbons from aqueous solutions thereof which comprises: (a) contacting said aqueous solutions for a time sufficient to extract said halogenated hydrocarbon with a phosphine oxide compound wherein said phosphine oxide compound has the formula:

$$R_3P=O$$

wherein the three R groups are each individually alkyl, cycloalkyl, aralkyl and substituted-aralkyl; and (b) separating the extracted aqueous solution from said phosphine oxide compound.

2. A method according to claim 1 wherein said phosphine oxide is on a solid support.

3. A method according to claim 2 wherein solid support material is a copolymer of at least one monovinyl compound and at least one polyvinyl compound.

4. A method according to claim 3 wherein said solid support material is divinylbenzene-cross-linked polystyrene.

5. A method according to claim 2 wherein said alkyl moiety is branched or linear and contains from about 6 to 18 carbon atoms and where said cycloalkyl moiety contains about 6 to 8 carbon atoms and is substituted or unsubstituted.

6. A method according to claims 1, 2, 3, 4 or 5 wherein said phosphine oxide compound is trialkylphosphine oxide.

7. A method according to claim 6 wherein said trialkylphosphine oxide is tri-n-octylphosphine oxide or tri-n-hexylphosphine oxide or a mixture thereof.

8. A method according to claim 2 wherein said inert, solid support material is a naturally occurring inorganic material.

9. A method according to claim 8 wherein said support material is diatomaceous earth.

10. A method according to claim 2 wherein said support material is silica gel.

11. A method according to claims 2, 3, 4 or 5 wherein said phosphine oxide compound is incorporated on said support material by impregnation.

12. A method according to claims 3 or 4 wherein said phosphine oxide compound is incorporated on said support by encapsulation.

* * * * *